(12) United States Patent
Buck et al.

(10) Patent No.: US 7,891,360 B2
(45) Date of Patent: Feb. 22, 2011

(54) EARPLUG AND MANUFACTURING METHOD

(75) Inventors: Karl Buck, Bartenheim (FR); Markus Christoph, Lörrach-Haagen (DE)

(73) Assignee: Institut Franco-Allemand de Recherches de Saint-Louis, Saint Louis Cedex (FR)

( * ) Notice: Subject to any disclaimer, the term of this patent is extended or adjusted under 35 U.S.C. 154(b) by 249 days.

(21) Appl. No.: 11/474,326

(22) Filed: Jun. 26, 2006

(65) Prior Publication Data

US 2007/0000499 A1    Jan. 4, 2007

(30) Foreign Application Priority Data

Jun. 25, 2005    (DE) .................. 10 2005 029 514

(51) Int. Cl.
*A61F 11/00* (2006.01)
*A61F 11/06* (2006.01)

(52) U.S. Cl. .................. 128/864; 381/72; 381/114; 381/151; 381/190; 381/328

(58) Field of Classification Search .............. 128/864; 381/114, 151, 173, 190, 328, 380, 312, 316, 381/322, 72, 337, 354; 181/128–130, 134, 181/135, 199

See application file for complete search history.

(56) References Cited

U.S. PATENT DOCUMENTS

| 4,150,262 | A |   | 4/1979  | Ono |
|-----------|---|---|---------|-----|
| 4,641,054 | A | * | 2/1987  | Takahata et al. ............ 310/324 |
| 4,696,045 | A |   | 9/1987  | Rosenthal |
| 4,867,149 | A | * | 9/1989  | Falco .......................... 128/864 |
| 4,975,967 | A |   | 12/1990 | Rasmussen |
| 5,345,509 | A | * | 9/1994  | Hofer et al. .................. 381/326 |
| 6,643,378 | B2| * | 11/2003 | Schumaier ................... 381/326 |
| 6,741,719 | B1| * | 5/2004  | Orten .......................... 381/380 |

FOREIGN PATENT DOCUMENTS

| DE | 28 10 716 A1 | 9/1979 |
| DE | 28 49 152 B1 | 4/1980 |
| DE | 39 16 995 A1 | 12/1989 |

* cited by examiner

*Primary Examiner*—Patricia M Bianco
*Assistant Examiner*—Keri J Nicholson
(74) *Attorney, Agent, or Firm*—Oliff & Berridge, PLC

(57) ABSTRACT

An earplug that includes a piezoelectric element that converts electrical signals into oscillations; and a deformable material of which at least one segment is insertable into an external auditory canal of a person to ensure an acoustic seal by deformation, the piezoelectric element being disposed inside the deformable material and in fixed contact therewith, the deformable material being able to transmit the oscillations at a periphery and ensure conduction of the oscillations through cartilage and soft tissue of the auditory canal.

10 Claims, 2 Drawing Sheets

EARPLUG AND MANUFACTURING METHOD

INCORPORATION BY REFERENCE

The disclosure of German Patent Application No. 10-2005-029-514.2 filed on Jun. 25, 2005, including the specification, drawings and abstract, is incorporated herein by reference in its entirety.

BACKGROUND

The invention relates to the area of ear protection devices, specifically an earplug provided with a piezoelectric element that converts electrical signals into oscillations. The invention also relates to various methods for manufacturing these earplugs.

Earplugs, which serve both for auditory protection and for listening, have numerous applications. As one widely used principle, an earplug has an electroacoustic converter on one of its front parts. In order for the sound waves to reach the eardrum, the earplug has an interior canal that transmits the sound from the acoustic converter to the eardrum through the air. This principle, with a small loudspeaker and a canal open on one side, enables sound to be conducted through the air, as already presented in DE 39 16 995 C2 for example. These earplugs with a built-in listening device often have excellent acoustic properties, but their design is very complicated so that they are very expensive to manufacture. For better understanding, it will be noted that the aforementioned earplugs also have a device enabling them to be used also as microphones.

DE 28 49 152 B1 presents an earplug in the same family provided with a piezoelectric element that converts the electrical signals into oscillations. In other words, the piezoelectric element is designed to operate in a listening mode. The piezoelectric element also acts as a microphone. The earplug has a rigid housing in the shape of a hard metal or plastic plug designed to be inserted into the external auditory canal. The piezoelectric element with a weight is mounted in the cavity of the housing like a built-in beam. The aim is to reduce feedback effects when the piezoelectric element is used as a microphone.

There also exists earplugs with a piezoelectric element described solely for microphone use. In this regard, mention will be made of patents in which the piezoelectric element is built into a rigid body such as in DE 2810716 for example, or a semi-soft body made of RTV silicone rubber but stiffened by a spring as in U.S. Pat. No. 4,696,045 for example, the spring also serving to protect the piezoelectric element. In operation, the user's voice is conducted from his throat to the bones of the head, then through the wall of the auditory canal. Hence, it is transmitted by bone conduction. The use of a rigid body or semi-soft body stiffened by a spring is unpleasant, even irritating or painful, for the user.

SUMMARY

Such earplugs have drawbacks and are not designed to function as listening devices.

The present invention thus proposes an earplug with a piezoelectric element that converts electrical signals into oscillations, that is simple in design, is inexpensive to manufacture, and has no unpleasant or painful sensations for the user.

According to one exemplary aspect, an earplug includes a piezoelectric element that converts electrical signals into oscillations and made of a deformable material of which at least one part, called a segment, is insertable into an auditory canal of a person to ensure an acoustic seal because of its deformability, the piezoelectric element being disposed inside deformable material and in fixed contact therewith, the deformable material being able to transmit the oscillations at its periphery and to ensure conduction of these oscillations through the cartilage and soft tissues of the auditory canal wall.

The advantages obtained with the invention are that the costs of the earplug provided with a piezoelectric element for converting electrical signals into vibrations and acoustic oscillations are reduced by virtue of a simple design. In simple form, the piezoelectric element is in direct contact with the material of the earplug with which no stiffening elements are associated. This contact is fixed and transmits oscillations. The oscillations of the piezoelectric element are transmitted to the earplug. The earplug has a segment introduced into the external auditory canal and, because of the deformability of its material, is designed to ensure a circular seal inside the auditory canal. This contact between the earplug and the external auditory canal allows noise to be conducted mainly through the cartilaginous parts and soft tissues of which the wall of the auditory canal is made. Also, a secondary support effect occurs because the earplug, excited by the piezoelectric element, itself produces sound waves which are diffused by the earplug into the volume of enclosed air of the auditory canal and are transmitted to the eardrum.

According to one embodiment of the invention, the material of which the earplug segment is made is deformable by the oscillations of the piezoelectric element. The piezoelectric element, which is in fixed contact with the material of the earplug, deforms the material of the earplug. When it is inserted into the auditory canal of a person, the earplug segment transmits these deformations, which represent the oscillations, both to the soft and cartilaginous parts of the canal and to the volume of air enclosed inside the canal.

According to another embodiment of the invention, the material of which the segment is made is elastic and flexible. This reinforces the auditory protection function, because a good seal of the external auditory canal is obtained. Moreover, the desired noise conduction is also obtained. Contrary to the earplugs described in U.S. Pat. No. 4,696,045 and DE 2810716, in the earplug according to the invention, there is no bone conduction in the sense of these patents.

The use of an elastic and hence soft material allows the earplug to adapt perfectly inside the external auditory canal with no great stress on the latter and hence without producing an unpleasant or painful sensation as in the case where a rigid or stiffened semi-soft body is used, and enables oscillations to be transmitted only to the soft and cartilaginous parts of the canal.

According to another embodiment of the invention, the fixed contact with the deformable material of the segment is obtained by expansion or injection of plastic around the piezoelectric element. During the expansion or injection, the plastic is liquid and produces an assembly cemented to the surface of the piezoelectric element.

According to another embodiment of the invention, the piezoelectric element is embedded and/or cemented into a recess in the earplug segment. Once again, a fixed contact between the piezoelectric element and the material of the earplug is ensured.

According to another embodiment of the invention, the earplug is an earplug with lamellae. They are less expensive to manufacture. Moreover, it is simple to assemble a piezoelectric element in an earplug with lamellae.

According to another embodiment of the invention, the earplug is a personalized earplug adapted to the shape of an individual's external auditory canal. A personalized earplug can also readily be completed with a piezoelectric element.

According to one particular feature, the piezoelectric element is entirely disposed in a part of the earplug that cannot be inserted inside the auditory canal of a person.

The invention also relates to a first method of manufacturing an earplug according to the invention and is characterized by comprising the following steps: attaching the piezoelectric element inside a negative of an earplug, and expanding or injecting a liquid plastic around the piezoelectric element. One can thus manufacture an earplug with a built-in piezoelectric element at low cost.

The invention also relates to a second method of manufacturing an earplug according to the invention characterized by comprising the following steps: manufacturing the earplug with a recess adapted to a geometric shape of the piezoelectric element, embedding the piezoelectric element in the recess, and maintaining a bond by force-fitting and/or cementing the piezoelectric into the recess. This method lends itself readily to integration of a piezoelectric element into a so-called personalized earplug.

BRIEF DESCRIPTION OF THE DRAWINGS

Other advantages and features will appear from the description of several embodiments of the invention relating to the attached drawings wherein.

DETAILED DESCRIPTION OF EMBODIMENTS

Figure 1:
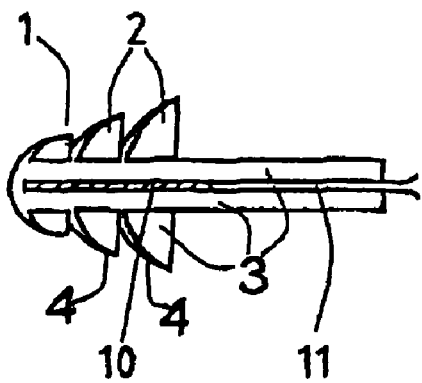
FIG. 1 shows an earplug provided with a piezoelectric element in the form of a schematic drawing viewed from the front in cross section according to a first embodiment of the invention.
Figure 2:
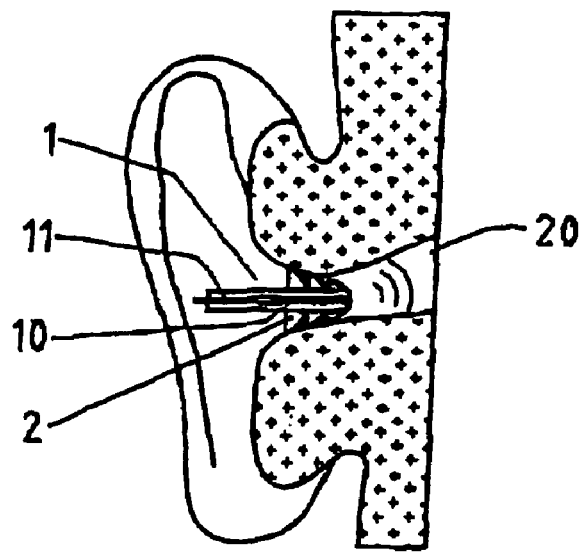
FIG. 2 shows schematically an earplug according to the first embodiment used in an auditory canal, in a front view in cross section.
Figure 3:
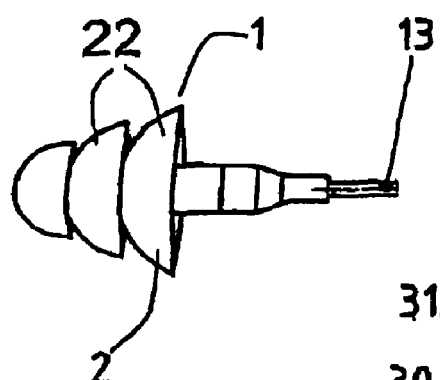
FIG. 3 shows schematically an earplug similar to that shown above, but oriented more to a manufacturing-ready product, in front view.

FIGS. 1 to 3 relate to an ear protector, designed as a lamellae type earplug 1. The lamellae 2 are shown in these figures.

As shown in FIG. 1, an earplug 1 has a piezoelectric element 10 that converts electrical signals into oscillations. In other words, the earplug 1 functions as a listening device. The piezoelectric element 10 is in fixed contact and transmits these oscillations to the material 3 of which the earplug 1 is made.

FIG. 2 best illustrates the operation of the earplug 1. The oscillations of the piezoelectric element 10 are transmitted to the earplug 1. The earplug 1 has a segment 22 with the lamellae 2 and is inserted into the external auditory canal 20 of a person and is designed to ensure a circular seal inside this auditory canal 20. With the contact between the lamellae 2 of the earplug 1 and the external auditory canal 20, noise is conducted through the cartilage and soft tissues of the auditory canal wall. This noise is transmitted and perceived by the inner ear. Also, a secondary support effect intervenes in that the earplug 1, excited by the piezoelectric element 10, produces sound waves that are diffused by the earplug 1 to the volume of air enclosed in the external auditory canal 20 and transmitted to the eardrum.

The material 3 of the earplug is deformable by the oscillations of the piezoelectric element 10 and is able to transmit these oscillations at a periphery 4. When the segment 22 of the earplug 1 is inserted into the external auditory canal 20 of an individual, its deformations, which represent the oscillations, are transmitted on the one hand to the soft and cartilaginous tissues of the external auditory canal 20, and on the other hand to the volume of air enclosed in the auditory canal 20. The material 3 of the earplug is elastic and flexible. The material 3 reinforces the auditory protection function, and a good seal of the external auditory canal is obtained. Also, noise conduction by the cartilage and soft parts of the auditory canal wall is obtained in this way.

Figure 4:
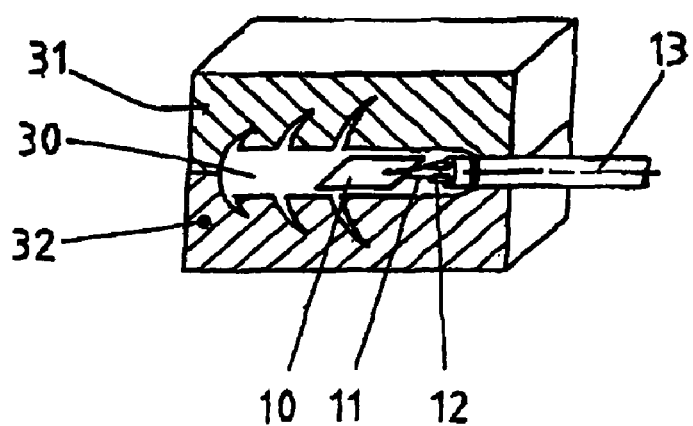
FIG. 4 shows a negative for injection of an earplug with a piezoelectric element around which plastic will be injected, in perspective section.

The fixed contact with the earplug material is obtained by injecting plastic around the piezoelectric element 10. Expansion of the plastic around the piezoelectric element 10 is a possible alternative. FIG. 4 shows the corresponding manufacturing of an earplug 1. Manufacturing includes the following steps:

Attaching a piezoelectric element 10 inside a negative 30 of an earplug 1. As shown, the piezoelectric element 10 is provided with two wires 11 that supply it with electrical signals, with the wires 11 being disposed inside a first sheath 12 made of an electrically insulating material, and the first sheath 12 being inside a second sheath 13, thus forming the cable line of the piezoelectric element 10; and Expanding or injecting a liquid plastic around the piezoelectric element 10.

The negative 30 is made of a first mold half 31 for injection molding and a second mold half 32 for injection molding. For reasons of simplicity, the injection molding details are not shown.

Figure 5:
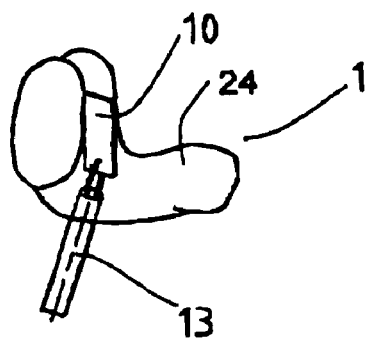
FIG. 5 shows schematically a personalized earplug, in perspective.
Figure 6:
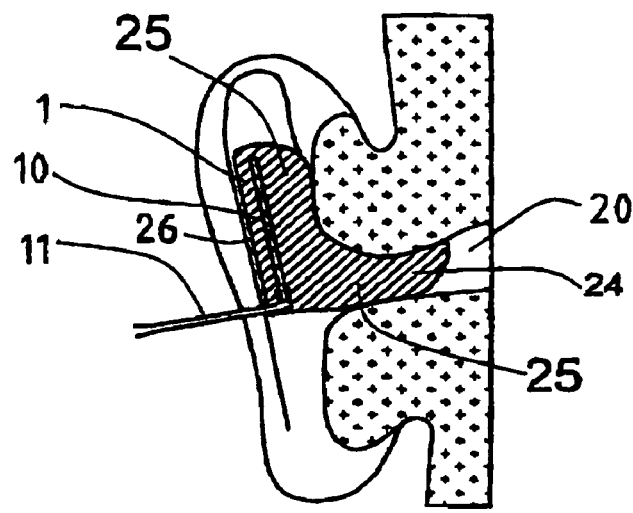
FIG. 6 shows a personalized earplug, similar to that of FIG. 5, used in an auditory canal, in the form of a schematic front view cross section.

FIGS. 5 and 6 relate to a personalized earplug 1 composed of a piezoelectric element 10 that converts electrical signals into oscillations and of a deformable material 25. The deformable material 25 has a first part 24, called a segment, that is capable of being insertable into the auditory canal of a person and ensuring an acoustic seal because of its deformability, and a second part 26 that is not insertable into the auditory canal of a person, with the piezoelectric element 10 being disposed inside the second part 26 and in fixed contact therewith. The shape of the first part 24 is adapted to the shape of the auditory canal 20 of a person. This first part 24 transmits the oscillations, produced by the piezoelectric element 10, primarily and chiefly by conduction through the cartilage and soft tissues of the external auditory canal and secondly by vibrations of the air located in the auditory canal 20. In addition it provides the acoustic seal of the external auditory canal into which it is inserted, as described above in relation to FIG. 2.

The piezoelectric element 10 is force-fitted and/or cemented in a recess in the earplug 1. This is achieved by the following steps:

Manufacturing an earplug 1 with a recess adapted to the geometric shape of the piezoelectric element 10; and Inserting the piezoelectric element 10 into the recess either by force-fitting and/or by cementing the piezoelectric element 10 into the recess.

Details of the earplug will be described below. This is done with models of the earplug such as those manufactured by the Applicants.

Figure 7:
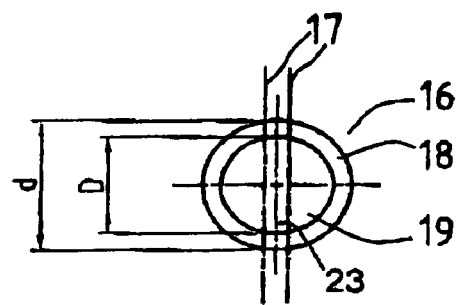
FIG. 7 shows a commercial piezoelectric element in front view.
Figure 8:
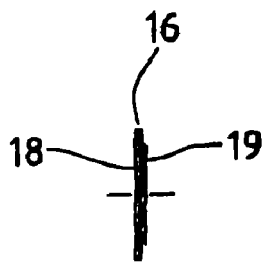
FIG. 8 shows the commercial piezoelectric element in FIG. 7, in a side view cross section.

Manufacturing of the earplug model begins with a commercially available piezoelectric element 16. FIGS. 7 and 8 show such a piezoelectric element 16.

The following information is available for the piezoelectric element 16:

Design: the piezoelectric element 16 is a component in which a ceramic piezoelectric disk 19 is disposed on a circular brass disk 18. The ceramic piezoelectric disk 19 has a diameter D of 15 mm and a thickness of 0.2 mm, as shown in FIG. 7. The diameter d of the brass disk is 20 mm and its thickness is 0.23 mm;

Technical parameters:
Resonance frequency: 6.4 kHz,
Resonance impedance: 200 Ohm (note: the Applicants have measured higher values),
Capacitance: 12 nF; and Reference:
The piezoelectric element 16 may be obtained under the designation EPX-20MS64, item number 712918-U4, from the mail order company Conrad Electronic.

Figure 9:
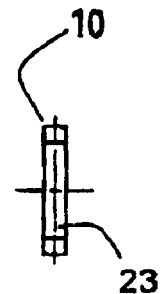
FIG. 9 shows the piezoelectric element usable for an earplug, cut out from the commercial piezoelectric element, in front view.

Since the commercial piezoelectric element 16 was too large for direct assembly, a segment 23 of the latter was cut out to make an earplug model. FIG. 7 has two thick, dashed lines 17 illustrating the cutting lines of the segment 23. The cut-out segment 23 is shown in FIG. 9. It is the resulting piezoelectric element 10 that is usable for manufacturing an earplug model.

The manufacture of a first model will first be described. It is a lamellae type earplug whose principle is shown in FIGS. 1 to 3. The starting point is a commercially available earplug. This may be procured commercially under the name UltraFit® Earplugs—Aearo E.A.R®. Manufacture consists of the following steps:

creation of a lengthwise bore 2 mm in diameter;
insertion of the piezoelectric element 10 shown in FIG. 9; and
cementing this piezoelectric element 10 with silicone.

Manufacture of a second model, which is a personalized earplug of which the principle is shown in FIGS. 5 and 6, will now be described. The starting point is a commercially available earplug. It is sold by the company Sonomax Hearing Healthcare Inc. under the name SonoCustom®. The SonoCustom® earplug has a rubber envelope outside and hardened silicone inside. The silicone has been injected in liquid form into the rubber envelope while the rubber envelope is in the auditory canal of a person. Once the silicone has hardened, the personalized earplug with a rubber envelope has been produced. Integration of the piezoelectric element is done in the following steps:

Cutting of a slot with a blade;
Insertion of the piezoelectric element 10 shown in FIG. 9; and
Cementing this piezoelectric element 10 with silicone.

What is claimed is:

1. An earplug, comprising:
   a piezoelectric element that converts electrical signals into oscillations; and
   a deformable material of which at least one segment is insertable into an external auditory canal of a person to ensure an acoustic seal by deformation, the piezoelectric element being disposed inside the deformable material and in fixed contact therewith, the deformable material being able to transmit the oscillations at a periphery and ensure conduction of the oscillations through cartilage and soft tissue of the auditory canal without bone conduction through bones of a user's head.

2. The earplug according to claim 1, wherein the deformable material of which at least one segment is made can be deformed by the oscillations of the piezoelectric element.

3. The earplug according to claim 1, wherein the deformable material of which the segment is made is elastic and flexible.

4. The earplug according to claim 1, wherein the fixed contact with the deformable material is obtained by expansion or injection of plastic around the piezoelectric element.

5. The earplug according to claim 1, wherein the piezoelectric element is embedded and/or cemented in a recess of the segment.

6. The earplug according to claim 1, wherein the earplug is a lamellae earplug.

7. The earplug according to claim 1, wherein the earplug is a personalized earplug adapted to a shape of the auditory canal of the person.

8. The earplug according to claim 1, wherein the piezoelectric element is disposed entirely in a part of the earplug not insertable into the auditory canal of the person.

9. The earplug according to claim 1, wherein the piezoelectric element is in direct contact with the deformable material with which no stiffening elements are associated.

10. The earplug according to claim 1, wherein the deformable material is designed to ensure a circular seal inside the auditory canal.

* * * * *